(12) United States Patent
Bacher

(10) Patent No.: US 8,133,244 B2
(45) Date of Patent: Mar. 13, 2012

(54) MEDICAL INSTRUMENT

(75) Inventor: Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 911 days.

(21) Appl. No.: 12/170,497

(22) Filed: Jul. 10, 2008

(65) Prior Publication Data

US 2009/0018568 A1  Jan. 15, 2009

(30) Foreign Application Priority Data

Jul. 13, 2007  (DE) .......................... 10 2007 034 577

(51) Int. Cl.
*A61B 17/00* (2006.01)

(52) U.S. Cl. .............. 606/170; 606/1; 606/205

(58) Field of Classification Search .............. 606/79, 606/139, 167, 170–180, 205; 600/562, 564; 604/108, 109; 128/90.48; 285/314–316
See application file for complete search history.

(56) References Cited

U.S. PATENT DOCUMENTS

| | | | | |
|---|---|---|---|---|
| 5,176,702 A * | 1/1993 | Bales et al. | ...... | 606/208 |
| 5,472,439 A * | 12/1995 | Hurd | ...... | 606/171 |
| 5,893,835 A * | 4/1999 | Witt et al. | ...... | 606/205 |
| 6,689,072 B2 * | 2/2004 | Kaplan et al. | ...... | 606/167 |
| 7,758,591 B2 * | 7/2010 | Griego et al. | ...... | 606/113 |
| 2004/0153101 A1 * | 8/2004 | Bolduc et al. | ...... | 606/143 |

FOREIGN PATENT DOCUMENTS

| | | |
|---|---|---|
| CA | 2212768 C | 8/1996 |
| DE | 4101472 C2 | 7/1992 |
| DE | 19740847 C1 | 8/1999 |
| DE | 69419996 T2 | 2/2000 |
| DE | 69635050 T2 | 5/2006 |
| EP | 0647433 A1 | 4/1995 |
| WO | 9420037 A1 | 9/1994 |
| WO | 9624296 A1 | 8/1996 |
| WO | 9639944 A1 | 12/1996 |

OTHER PUBLICATIONS

German Search Report, Jan. 1, 2006, 4 Pages.
European Search Report; Application No. EP 08 01 1822; Jun. 25, 2010; 4 pages.

* cited by examiner

*Primary Examiner* — Kathleen Sonnett
*Assistant Examiner* — Sarah Webb
(74) *Attorney, Agent, or Firm* — St. Onge Steward Johnston & Reens LLC

(57) ABSTRACT

A medical instrument has a shaft. The shaft has an outer shaft and an inner shaft. The outer shaft encloses the inner shaft. The medical instrument further has an actuator for rotating the inner shaft about a longitudinal axis relative to the outer shaft, arranged at a proximal end region of the shaft. The medical instrument has at least two tappet elements for transferring a rotary movement of the actuator to the inner shaft, which are engaged interchangeably with the inner shaft for transferring the rotary movement of the actuator to the inner shaft. The tappet elements reach through peripherally limited openings in a proximal end region of the outer shaft, which openings are offset with respect to one another in the longitudinal direction.

22 Claims, 12 Drawing Sheets

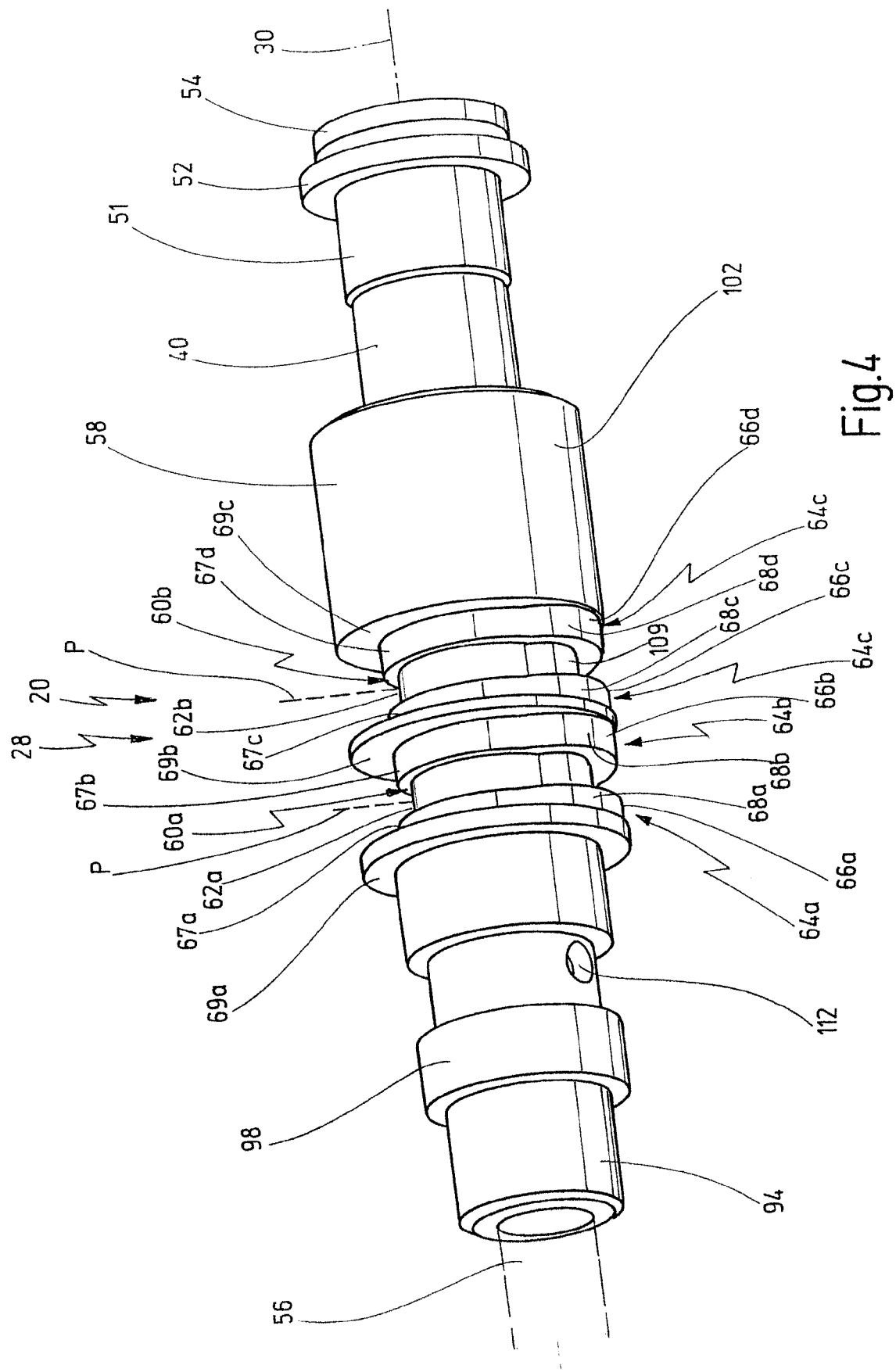

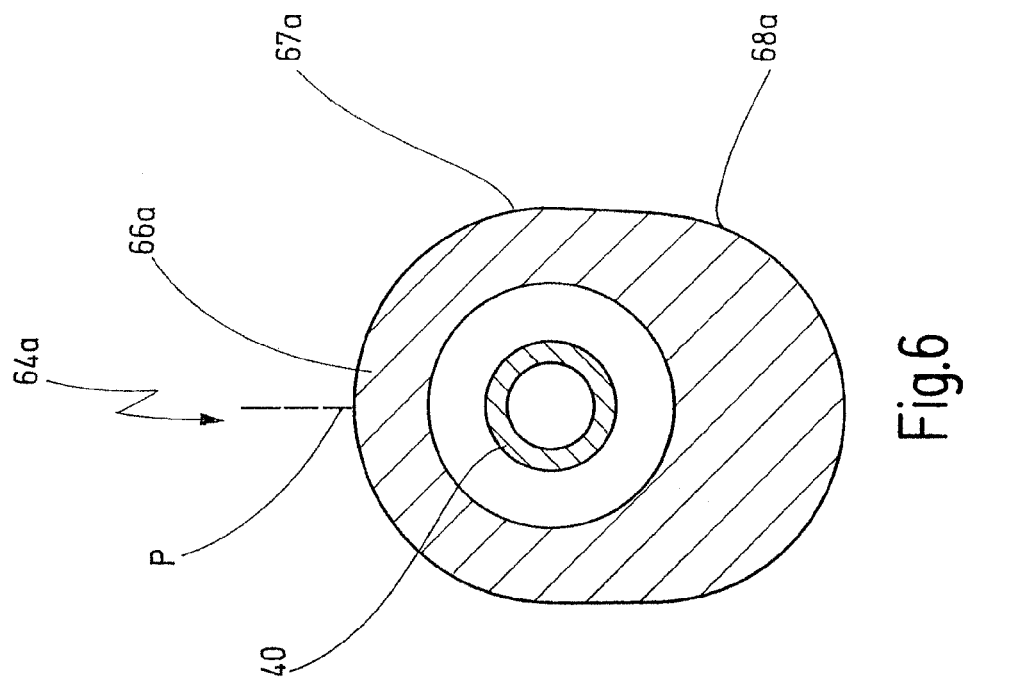
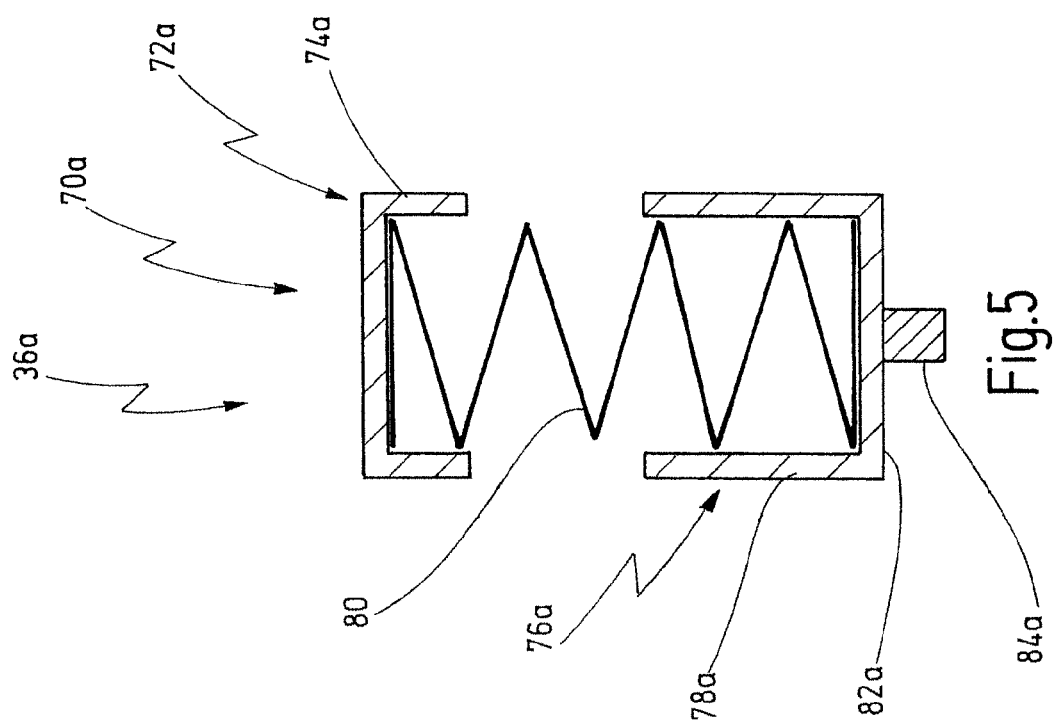

MEDICAL INSTRUMENT

CROSS REFERENCE TO RELATED APPLICATION

The present application claims priority of German patent application No. 10 2007 034 577.3 filed on Jul. 13, 2007.

BACKGROUND OF THE INVENTION

The invention generally relates to medical instruments. More specifically, the invention relates to medical instruments, having a shaft which has an outer shaft and an inner shaft, wherein the outer shaft encloses the inner shaft, and wherein the inner shaft is rotatable with respect to the outer shaft.

Medical instruments of the type initially described are used, for example, in minimally invasive surgery during a laparoscopic procedure to remove diseased tissue or also to atrophy previously sectioned tissue. For this purpose, a distal end region of the shaft of the medical instrument is inserted into a body cavity of a patient, on which corresponding gripping instruments, electrodes or the like are arranged. The shaft of the medical instrument is usually designed in two parts and has an inner shaft rotatable about the longitudinal axis of the medical instrument, which is housed in an outer shaft. The operation instruments are accordingly arranged on the distal end region of the inner shaft. The operation instruments are put in a position favourable for the procedure only after the shaft has been inserted into the operation area by rotation of the inner shaft relative to the outer shaft around the longitudinal axis of the medical instrument.

A medical instrument known from CA 2 212 768 A in form of a morcellator has an outer shaft, which encloses an inner shaft rotatable relative to it and is connected, such that it is rotationally fixed, to a proximal end of the handle of the medical instrument. The outer shaft extends as far as a distal end of the handle, while the inner shaft extends through the handle as far as a proximal end of the handle. A motor housed in the handle is connected, such that it is rotationally fixed, via a tappet element to the inner shaft. The tappet element has a gearwheel drive, which is connected, such that it is rotationally fixed, to a region of the inner shaft, arranged proximally to the proximal end of the outer shaft in order to rotate the inner shaft about the longitudinal axis.

Other medical instruments are generally known which have only an outer shaft, which is connected, such that it is rotationally fixed, to a handle. The outer shaft of the known instrument extends into the interior of the handle, and its proximal end region is screwed to the handle in the handle interior via a nut. The handle of the medical instrument can, for example, be a handle already available and normally capable of being used for operations in the area of minimally invasive surgery.

If it is planned to further develop such a medical instrument to the extent where, in addition to the outer shaft, it has an inner shaft inside the outer shaft which is rotatable about the longitudinal axis, the technical problem arises as to how corresponding torque transmission mechanics of the instrument could be designed which would allow relative rotation of the inner and outer shaft with simultaneous screwing of the outer shaft to the handle inside the handle.

A conceivable configuration of such a further developed medical instrument is based on arranging magnets on the actuator and in the proximal end region of the inner shaft, thereby transferring the rotary movement of the actuator to the inner shaft without contact through the proximal end region of the outer shaft.

With this configuration of the torque transmission mechanics there is the disadvantage, however, with this type of torque transmission of only minimal force transfer made to the inner shaft.

In a further configuration of the developed instrument the proximal end region of the outer shaft, which is arranged inside the handle, could be interrupted about its entire circumference in two parts, and the actuator could directly engage on the inner shaft in the vicinity of this interruption between the two parts of the outer shaft.

In this embodiment of the medical instrument it is a disadvantage, however, for both parts of the proximal end region of the outer shaft to have to be connected, such that it is rotationally fixed, to the handle.

Yet another configuration of the further developed medical instrument could be based on guiding the inner shaft completely through the handle and arranging the actuator on the proximal side outside the handle directly on the inner shaft. The outer shaft would hereby be housed in the handle interior and connected, such that it is rotationally fixed, to the handle.

This configuration of the medical instrument does however have the disadvantage of the medical instrument not being able to be operated with one hand by a user, since the actuator is arranged on the proximal side of the handle.

SUMMARY OF THE INVENTION

It is thus an object of the present invention to provide a medical instrument of the abovementioned type which has torque transmission mechanics acting, via the proximal end region of the outer shaft, on the inner shaft to reliably transfer a rotary movement of the actuator to the inner shaft.

According to the invention, a medical instrument is provided, comprising a shaft having a longitudinal axis and a proximal end region, the shaft having an outer shaft and an inner shaft, the outer shaft enclosing the inner shaft, an actuator for rotating the inner shaft about the longitudinal axis relative to the outer shaft, the actuator being arranged at the proximal end region of the shaft. At least two tappet elements are operatively connected with the actuator for transferring a rotary movement of the actuator to the inner shaft. The at least two tappet elements are engaged inter-changeably with the inner shaft for transferring the rotary movement of the actuator to the inner shaft. The at least two tappet elements reach through peripherally limited openings in the proximal end region of the shaft, the openings being offset with respect to one another in direction of the longitudinal axis.

The medical instrument according to the invention has an outer shaft the proximal end region of which is interrupted by peripherally limited openings which are axially spaced apart, through which at least two tappet elements reach. The tappet elements engage interchangeably with the inner shaft to transfer a rotary movement of the actuator to the inner shaft so that the inner shaft can be rotated relative to the outer shaft. According to the invention, "interchangeable engagement of the tappet elements with the inner shaft" is understood as the rotation of the actuator being conveyed to the inner shaft respectively by one tappet element, however at the time of transfer between torque transfer of two different tappet elements both tappet elements can be engaged with the inner shaft so as to secure the inner shaft in its relative rotation with respect to the outer shaft and to prevent unwanted rotation thereof. Complete rotation of the inner shaft relative to the outer shaft by 360° is caused here by a plurality of directly successive partial rotations of the inner shaft, facilitated in each case by one tappet element. It is possible in particular that the inner shaft of the medical instrument can be rotated in both directions of rotation about the longitudinal axis.

The result of configuring the proximal end region of the outer shaft with peripherally limited openings, through which the tappet elements extend, is that the proximal end region of the outer shaft is designed in one piece and extends over the torque transmission mechanics of the medical instrument, as a result of which the proximal end region of the outer shaft can be connected to an already present handle, without reconfiguring the latter. As a result, the medical instrument advantageously has minimal manufacturing costs.

Because the tappet elements of the medical instrument are arranged on the distal side of the proximal end of the outer shaft, it is further possible to also arrange the actuator on the distal side of the handle so that the medical instrument advantageously can be operated with one hand by a user.

In a preferred configuration of the invention, adjacent to the openings of the outer shaft the outer shaft has control cams for the tappet elements, which control cams serve for alternate disengagement and engagement of the tappet elements with the inner shaft.

The control cams arranged on the outer shaft axially adjacent to the openings effect detachable connection of the tappet elements with the inner shaft so that one of the tappet elements engages with the inner shaft only interchangeably to transfer the rotary movement. This advantageously enables structurally simple and compact construction of the medical instrument, since the outer shaft not only serves to protect the inner shaft from damage, but at the same time also serves for disengagement and engagement of the tappet elements. Also, the control cams advantageously provide a peripheral guide for the tappet elements. The control cams of the outer shaft can, for example, be designed as excenter cams whose outer faces are spaced at various distances radially from the inner shaft, when viewed in the peripheral direction of the shaft.

In a further preferred configuration of the invention, the control cams are designed such that they have a full circumference and in their sections which are not adjacent to the openings are distanced radially from the inner shaft such that the tappet elements are disengaged from the inner shaft.

The effect of this measure is that the outer surfaces of the control cams in the region of their sections which are not immediately adjacent to the openings are distanced radially from the inner shaft such that the tappet elements, guided through the control cams, are distant from the inner shaft in these sections. This disengages the tappet elements from the inner shaft, so that each tappet element effects only partial rotation of the inner shaft relative to the outer shaft and rotation of the inner shaft by 360° through the individual partial rotations of the respective tappet elements is enabled. Designing the control cams such that they have a full circumference also advantageously enables guiding of the tappet elements in the peripheral direction of the shaft around its full circumference, whereby the arrangement of the tappet elements is stable during rotation when viewed peripherally.

In a further preferred configuration of the invention, the tappet elements are arranged peripherally offset.

The advantage of this measure is that manufacture of the outer shaft of the medical instrument is particularly easy, since at a peripheral point of the outer shaft the axially offset openings of the outer shaft are arranged axially adjacent to one another. In addition, the weight of the tappet elements when viewed in the peripheral direction of the shaft are advantageously distributed evenly, allowing the medical instrument to be easily held by the user.

In a further preferred configuration of the invention, the tappet elements are designed in each case in two parts, wherein a first tappet element part and second tappet element part of the tappet elements are supplied with resilient force, wherein the first tappet element part and second tappet element part can be moved in a radial direction relative to one another.

The effect of this measure is that the tappet elements can be adjusted in length in a radial direction so that the expansion of the tappet elements adapts advantageously to the profile of the control cams and can be selectively shortened and lengthened during its disengagement and engagement. In a configuration of the medical instrument in which tappet element ends are accommodated in the actuator, the length adjustable configuration of the tappet elements further enables those tappet elements not directly engaging with the inner shaft to be shortened and as a result not to protrude from the actuator. This advantageously ensures particularly secure operating of the medical instrument.

Alternatively and just as advantageously the tappet elements can also be configured in one piece, wherein the tappet elements can be engaged and disengaged by way of positive control with the inner shaft. Such positive control can be realised for example by guides which move the tappet elements in direction of the middle axis or away therefrom by engaging the tappet elements from the side.

In a further preferred configuration of the invention, the tappet elements extend in a radial direction with respect to the shaft.

The advantage of this measure is that the medical instrument in the vicinity of the torque transmission mechanics is designed to be particularly stable and compact, since the inner shaft, the outer shaft and the actuator can be arranged particularly close to one another. Also, the radial arrangement of the tappet elements with respect to the shaft causes a particularly large lever effect between the actuator and the inner shaft and thus a particularly effective torque transfer to the inner shaft, as a result of which advantageously only minimal force needs to be exerted onto the actuator to rotate the inner shaft. In one configuration of the actuator this is particularly advantageous as a manually actuated hand wheel, since the handle of the instrument can be held by the user in one hand and at the same time the actuator can be rotated without substantial exertion of force.

In a further preferred configuration of the invention the inner shaft has at least one recess for accommodating the tappet elements.

Providing a recess in the inner shaft advantageously enables engagement of the tappet elements with the inner shaft in a structurally very simple manner, since a tappet element end can engage directly in the recess. Also, direct engaging of the tappet elements in the recess of the inner shaft enables cost-effective manufacturing of the medical instrument, since no additional components need to be present to produce the rotationally fixed connection of the actuator and the inner shaft.

In conjunction with the peripherally offset arrangement of the tappet elements, the inner shaft preferably has a plurality of correspondingly peripherally offset recesses, in which in each case one or alternatively a plurality of tappet elements can engage, respectively.

In a further preferred configuration of the invention, the recess is designed as a groove running in the longitudinal direction.

This measure advantageously enables particularly simple and cost-effective manufacturing of the inner shaft, in that, for example, the groove is milled on the surface from an inner shaft wall. The axial configuration of the groove also advantageously enables secure holding of the tappet elements, since the tappet element ends engaging in the groove cannot slip, when viewed in a peripheral direction of the shaft. With respect to an axially adjacent arrangement of the axially offset tappet elements, the configuration of the recess as a groove enables alternate engaging of the tappet elements in a single recess, whereby the medical instrument is advantageously designed structurally very simply and at the same time can be manufactured cost-effectively.

The recess of the inner shaft can also be configured as a hole or depression of any shape reaching in through the inner shaft, the cross-section of which hole or depression is adapted to a tappet element end engaging in the recess.

In a further preferred configuration of the invention the openings of the outer shaft are designed as slots.

A configuration of the openings as, for example, oblong slots provides a peripheral guide for the tappet elements reaching in through the slots, whereby the tappet elements are advantageously mounted such that they are axially positionally stable, preventing them from tilting axially. This measure further enables particularly easy manufacture of the outer shaft, since peripherally limited elongated slots in the outer shaft can be incorporated particularly easily. The peripheral expansion of the slots is determined by the peripheral outer shaft partial regions required for stability of the outer shaft, which in each case connect to the slots when viewed peripherally.

In a further preferred configuration of the invention, the medical instrument has exactly two tappet elements, wherein the openings of the outer shaft are designed approximately semi-peripherally.

The configuration of the medical instrument with only two tappet elements represents the easiest possibility of producing torque transmission mechanics for rotating the inner shaft relative to the outer shaft, whereby the medical instrument is advantageously manufactured such that it is structurally very simple and with few components, and manufacturing costs of the medical instrument are also less in comparison with a configuration of the torque transmission mechanics with more than two tappet elements. Relative rotation of the inner shaft with respect to the outer shaft about an angle of 360° is hereby exerted by two partial rotations of the inner shaft in each case about an angle of 180°, which is achieved in each case by engaging one of the two tappet elements with the inner shaft.

In a further preferred configuration of the invention the two tappet elements are arranged offset peripherally by approximately 180°.

The advantage of this measure is that the rotary forces acting on the inner shaft engage on two opposite points of the inner shaft, when viewed in the peripheral direction of the shaft, whereby the rotary movement of the inner shaft is advantageously particularly uniform. In an arrangement of both tappet elements offset peripherally by approximately 180°, the medical instrument preferably has exactly two recesses, in which in each case one end of a tappet element pointing to the inner shaft alternately engages.

In a further preferred configuration of the invention, the two tappet elements are arranged axially adjacent.

In an axially adjacent arrangement of the two tappet elements, both tappet elements are arranged approximately on the same peripheral point of the shaft. The advantage of this measure is that the medical instrument can be manufactured particularly cost-effectively, since the inner shaft needs to have only one recess for both tappet elements. The openings of the outer shaft are hereby arranged peripherally offset by 180° and the control cams of the outer shaft are further designed such that they counterrotate and are likewise arranged offset by 180°.

Further advantages and features will emerge from the following description and the attached drawings.

It goes without saying that the abovementioned features and those yet to be explained hereinbelow can be used not only in the specified combinations, but also in other combinations or singly, without departing from the scope of the present invention.

BRIEF DESCRIPTION OF THE DRAWINGS

The invention will be explained hereinbelow in greater detail by means of several selected embodiments in conjunction with the attached drawing, in which:

FIG. 4 shows a perspective view of a proximal end of an outer shaft of the medical instrument in FIG. 1;

FIG. 5 shows a cross-sectional view of a tappet element;

FIG. 6 shows a cross-sectional view of a control cam;

DETAILED DESCRIPTION OF PREFERRED EXEMPLARY EMBODIMENTS

Figure 1:
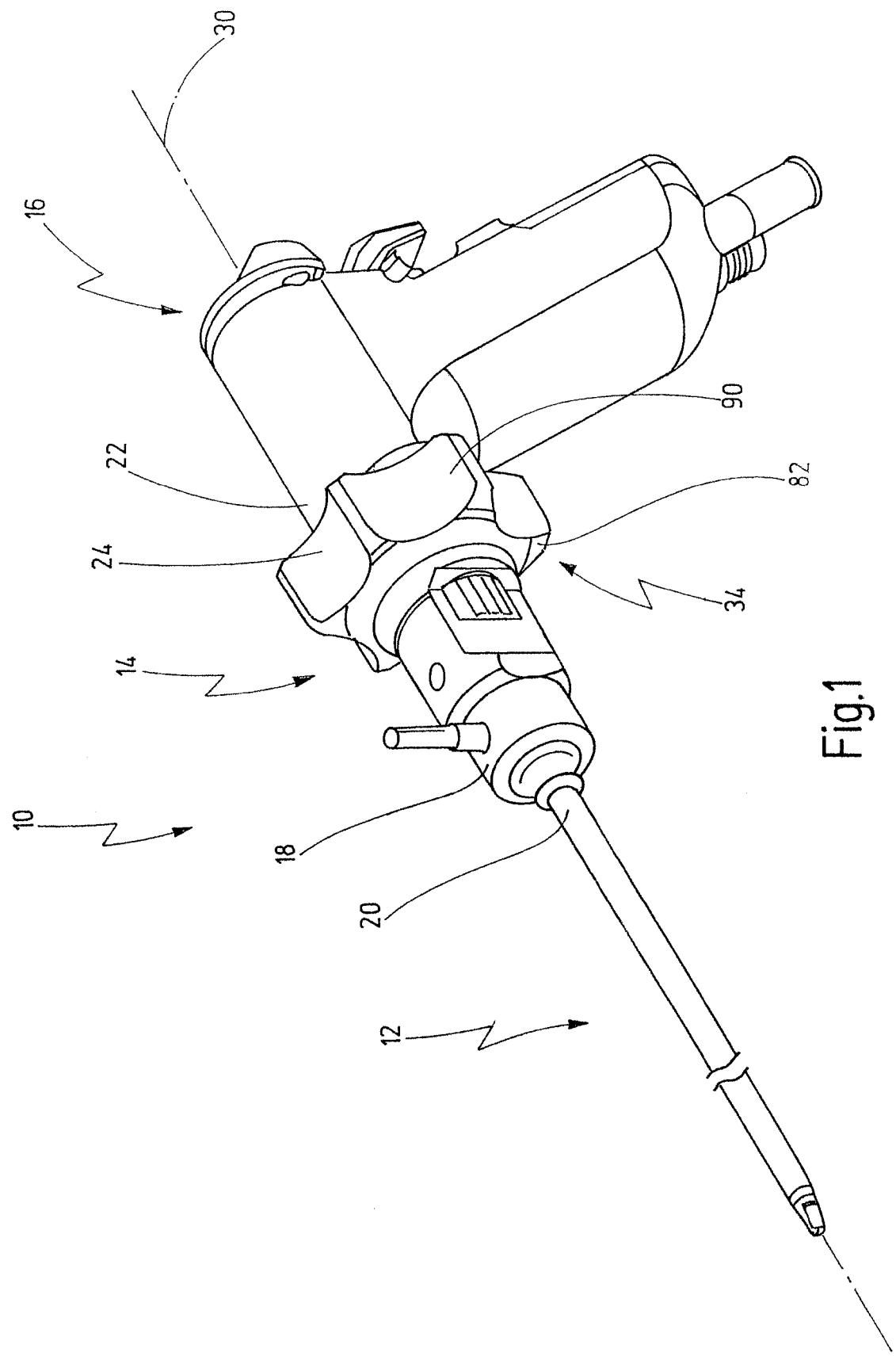
FIG. 1 shows a perspective view of a medical instrument according to the invention.

FIG. 1 illustrates a medical instrument provided with the general reference numeral 10. Further details of the medical instrument 10 are shown in FIGS. 2 to 9C.

The medical instrument 10 is used, for example, in the field of minimally invasive surgery during a laparoscopic procedure for atrophying sectioned tissue of a patient or for removing diseased tissue of the patient.

The medical instrument 10 has a shaft 12, a coupling element 14 and a handle 16. A distal end region 18 of the coupling element 14 is connected to a proximal end region 20 of the shaft 12 and a distal end region 22 of the handle 16 is connected to a proximal end region 24 of the coupling element 14.

Figure 2:
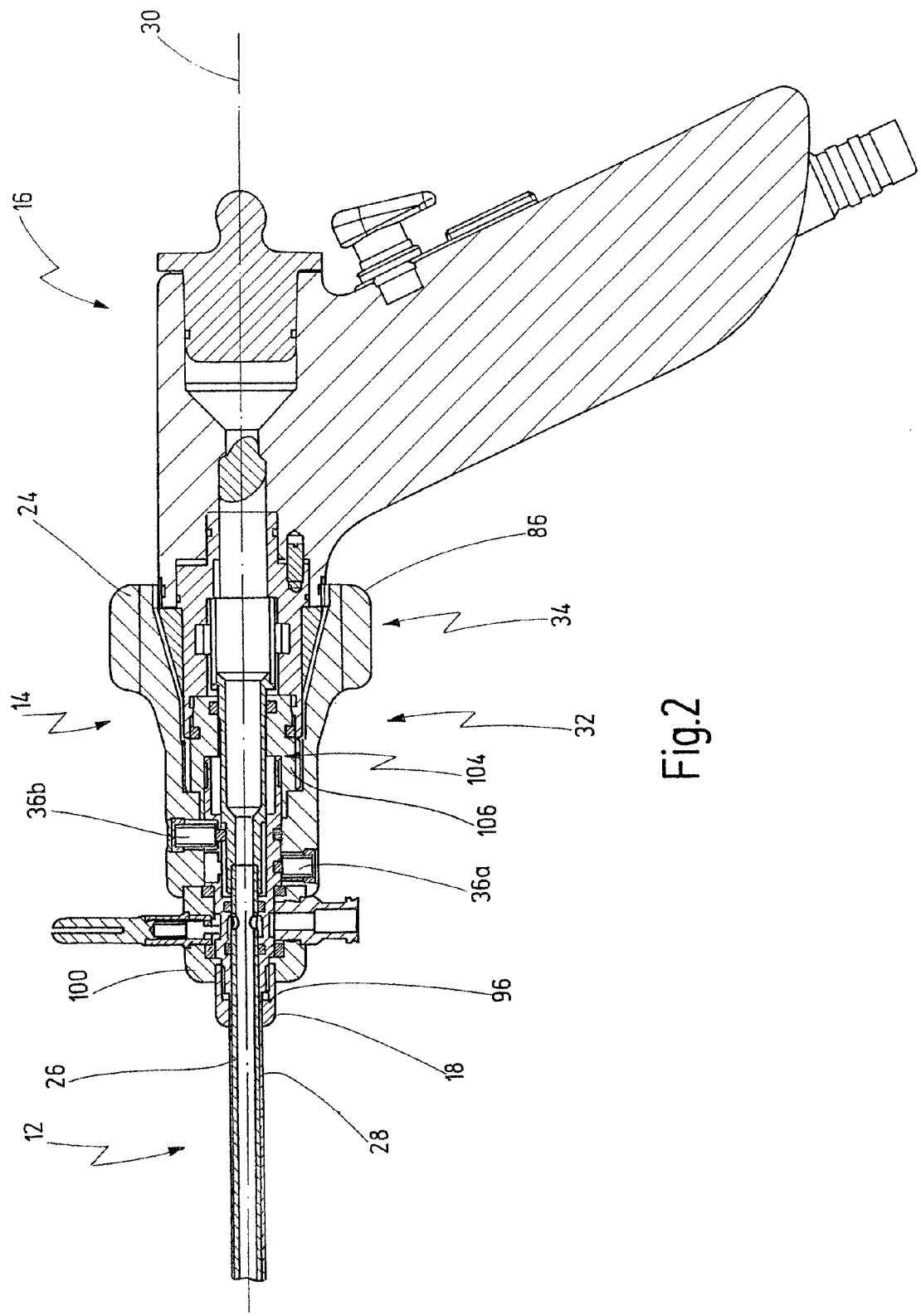
FIG. 2 shows a cross-sectional view of a handle of the medical instrument in FIG. 1.

As shown in FIG. 2, the shaft 12 is designed in two parts, and it has a respectively tubular inner shaft 26 and outer shaft 28. The inner shaft 26 is housed in the outer shaft 28 and designed such that it can rotate relative to the outer shaft 28 about a longitudinal axis 30 of the medical instrument 10 in both directions of rotation in each case about 360°. In the exemplary embodiment shown, the longitudinal axis 30 of the medical instrument 10 corresponds to a longitudinal axis of the shaft 12. The outer shaft 28 is connected, such that it is rotationally fixed, to the coupling element 14. It is likewise possible that the outer shaft 28 can be rotated for example stiffly about the longitudinal axis 30 and the inner shaft 26 can be rotated relative to the rotatable outer shaft 28.

To produce a relative rotary movement of the inner shaft 26 and of the outer shaft 28 the coupling element 14 has torque transmission mechanics 32 with an actuator 34 and at least two tappet elements 36, here exactly two tappet elements 36a, b, which are in each case alternately engaged with the inner shaft 26 to transfer the relative rotary movement.

With reference to FIGS. 3-7 the inner shaft 26, the outer shaft 28, the tappet elements 36a, b and the actuator 34 are described in greater detail hereinbelow.

Figure 3:
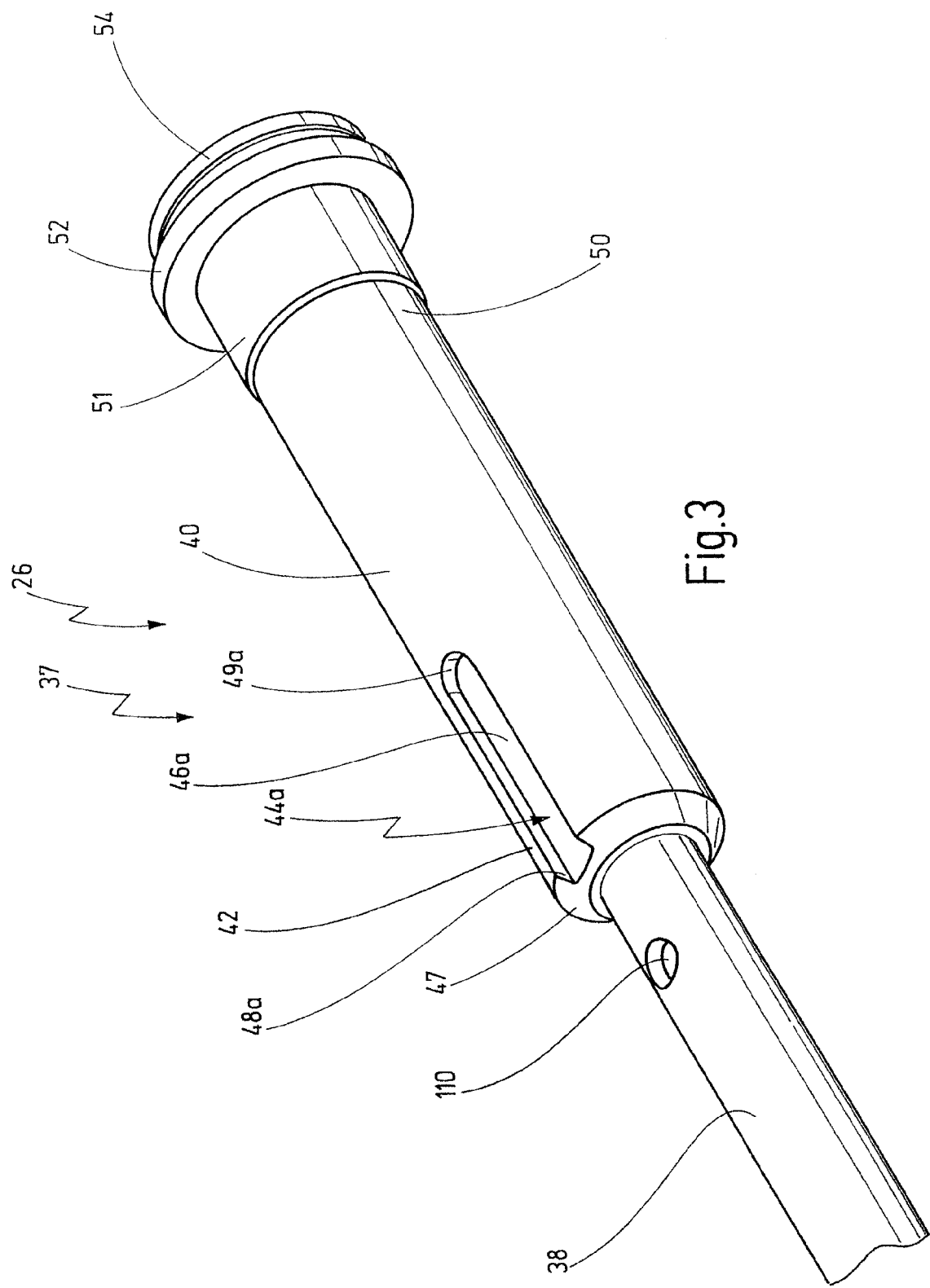
FIG. 3 shows a perspective view of a proximal end of an inner shaft of the medical instrument in FIG. 1.

As shown in FIG. 3, a proximal end region 37 of the inner shaft 26 is in two parts and has an inner tube 38 and a tubular inner tube holder 40, which are connected to one another such that they are rotationally fixed, for example by welding, and where required also soldering, on the proximal side or on the distal side. The inner tube 38 and the inner tube holder 40 can also be designed in one piece. The outer diameter of the inner tube 38 is smaller than the outer diameter of the inner tube holder 40 by approximately half, so that the inner shaft 26 widens gradually in the region of the transition between the inner tube 38 and the inner tube holder 40. In a distal end region 42 of the inner tube holder 40 two recesses 44a, b are provided, which are offset with respect to one another peripherally by approximately 180° and in the form of two axially limited grooves 46a, b running in the longitudinal direction 30 of the medical instrument 10. A distal end 47 of the distal end region 42 of the inner tube holder 40 is distally chamfered around its entire periphery so that the distal end 47 of the inner tube holder 40 tapers distally and a distal end 48a, b of the grooves 46a, b is open or has no wall. A proximal end 49a, b of the grooves 46a, b is designed semi-circularly. The grooves 46a, b are milled, for example, from the distal end region 42 of the inner tube holder 40. Here, a wall thickness of the distal end region 42 of the inner tube holder 40 is designed to be larger than the wall thickness of the inner tube 38 and of a remaining section of the inner tube holder 40, since the inner diameter of the inner tube 38 corresponds approximately to the inner diameter of the inner tube holder 40 in the region of the grooves 46a, b (cf. FIG. 7). An interior of the inner tube holder 40 widens out further proximally in a funnel shape so that the inner diameter of the inner tube holder 40 increases gradually and the inner tube holder 40 and the inner tube 38 have an approximately identical wall thickness, except in the region of both grooves 46a, b. The recesses 44a, b can also be designed as holes or as depressions of any desired shape reaching in through the inner tube holder 40.

Arranged at a proximal end region 50 of the inner tube holder 40 is a flange 51, a collar 52 and another flange 54. The outer diameter of the flange 54 or the outer diameter of the flange 51 is larger than the outer diameter of the flange 51 or the outer diameter of the inner tube holder 40. The outer diameter of the collar 52 is larger than the outer diameter of the flange 54.

The outer shaft 28 is likewise designed in two parts and has an outer tube 56 and an outer tube holder 58, which are connected to one another, such that they are rotationally fixed, on the proximal side or on the distal side (cf. FIG. 4). Likewise as for the inner tube 38 and the inner tube holder 40, the outer tube 56 and the outer tube holder 58 can be designed in one piece. The outer tube holder 58 has approximately in the middle two openings 60a, b in the form of two approximately semi-peripheral oblong slots 62a, b, which are arranged axially adjacent at approximately the same peripheral point of the outer tube holder 58. The slots 62a, b can also have an opening range of approximately 220° or also approximately 270°, when viewed in the peripheral direction of the shaft 12. The maximal opening range of the slots 62a, b is hereby determined by a minimal tube region partial circumference necessary for stability of the outer tube holder 58, which is arranged peripherally adjacent to the slots 62a, b. The wall thickness of the outer tube holder 58 in the region of both slots 62a, b is less than the wall thickness of the outer tube holder 58 in its region peripherally offset with respect to the slots 62a, b. The distal-side inner diameter of the outer tube holder 58 corresponds approximately to the outer diameter of the inner tube 38. An interior of the outer tube holder 58 widens out further gradually proximally so that the inner diameter of the outer tube holder 58 in the region of the slots 62a, b corresponds approximately to the outer diameter of the inner tube holder 40.

The outer tube holder 58 also has two control cams 64a-d on both sides of the two slots 62a, b respectively, which engage around the outer tube holder 58 around its entire periphery and are arranged adjacent to one another axially. As shown in FIG. 5, the control cams 64a-d are designed as excenter cams 66a-d running symmetrically with respect to one another. In the region of both slots 62a, b the excenter cams 66a-d correspond to an outer face of the tubular outer tube holder 58. The radial distance of the full outer faces 67a-d of the excenter cams 66a-d from the inner tube holder 40 varies in the peripheral direction of the shaft 12 to enable disengagement and engagement of the tappet elements 36a, b with the grooves 46a, b. In the region of the slots 62a, b the radial distance of the outer faces 67a-b from the inner tube holder 40 is approximately constant, while the radial distance from sections 68a-d, which are not immediately adjacent to the slots 62a, b, of the outer faces 67a-d of the excenter cams 66a-d from the inner tube holder 40 in this region increases with the distance from the slots. The sections 68a-d of the outer faces 67a-d of the excenter cams 66a-d have, in a region peripherally offset by approximately 180° with respect to a slot middle point P, the greatest radial distance from the inner tube holder 40.

The outer tube holder 58 further has three annular guide elements 69a-c for the tappet elements 36a, b, of which the approximately constant outer diameter is greater than the outer diameter of the outer tube holder 58. The first guide element 69a is arranged on the distal side directly adjacent to the cam 66a, the second guide element 69b is arranged between the cams 66b, c and the third guide element 69c is arranged on the proximal side directly adjacent to the excenter cam 66d. It is also possible that the excenter cams 66b, c are arranged directly adjacent to one another and the outer tube holder 58 has only the two guide elements 69a, c.

The tappet elements 36a, b are designed as cylindrical pins 70a, b in two parts, which extend in a radial direction of the shaft 12 (cf. FIG. 5). A first tappet element part 72a, b is designed as a cap 74a, b and a second tappet element part 76a, b is designed as a hollow-cylindrical lower part 78a, b. Between the cap 74a, b and the lower part 78a, b a spring 80a, b is housed so that the pins 70a, b can be shifted longitudinally in the radial direction of the shaft 12. Also, each lower part 78a, b has on its front end 82a, b, which front end is pointing towards the inner shaft 26 when the medical instrument 10 is in the assembled state, an oblong cylindrical extension 84a, b.

Figure 7:
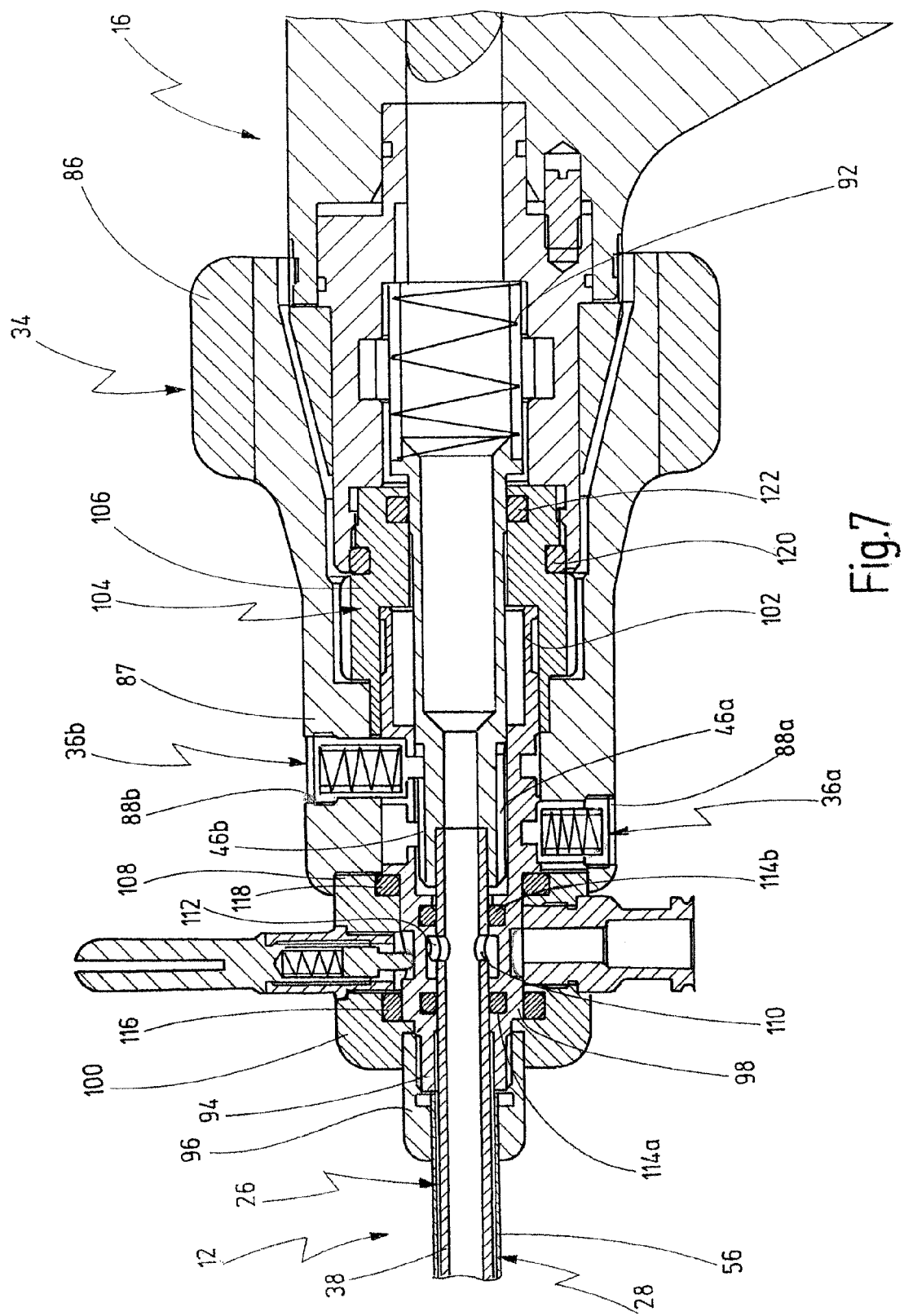
FIG. 7 shows an enlarged cross-sectional view of the handle in FIG. 2.

As shown in FIG. 7, the actuator 34 is designed as a hand wheel 86, in which the proximal end region 20 of the shaft 12 is housed. In a distal end region 87 of the hand wheel 86 are two bores 88a, b in the longitudinal direction 30 and peripherally offset with respect to one another by approximately 180°. The hand wheel 86 also has wing-like hollows 90 which a user can grip.

The inner tube 38, the inner tube holder 40, the outer tube 56, the outer tube holder 58, the tappet elements 36a, b, the control cams 64a-d and the actuator 34 are preferably made of rust-resistant metal, for example.

FIG. 7 shows the medical instrument 10 in its assembled state, in which the inner shaft 26 is housed in the outer shaft 28. Here, the distal end 47 of the inner tube holder 40 rests against the gradually widened region of the interior of the outer tube holder 58. A spring 92 is housed between the proximal end region 50 of the inner tube holder 40 and the handle 16. The spring 92 presses on the proximal side on the collar 52 of the inner tube holder 40, so that the inner shaft 26 is arranged axially and positionally stably with respect to the outer shaft 28.

A distal end region 94 of the outer tube holder 58 is connected, such that it is rotationally fixed, to a connector 96 of the coupling element 14, for example by screwing from the outside. The connector 96 and a region 98 of the outer tube holder 58, this region bordering the distal end region 94 of the outer tube holder 58, are further connected, such that they are rotationally fixed, to a connecting piece 100 of the coupling element 14, for example by screwing. The connecting piece 100 can have attachments for suction or irrigation pipes or also a high-frequency current terminal for an electrode, which electrode can be arranged at a distal end of the shaft 12. A proximal end region 102 of the outer tube holder 58 is also connected, such that it is rotationally fixed, to the handle 16 via a connecting element 104 on the inside. The connecting element 104 can, for example, be a nut 106 which can be screwed to the handle 16.

The inner tube holder 40 is connected, such that it is rotationally fixed, to the hand wheel 86 via the tappet elements 36a, b such that rotation of the hand wheel 86 is transferred directly to the inner tube holder 40 and the inner tube 38, which is connected to the inner tube holder 40 such that it is rotationally fixed, revolves relative to the outer shaft 28. On the inside the hand wheel 86 is spaced radially from the handle 16, the connecting element 104 and the outer tube holder 58 such that no frictional forces occur on these components which might impair rotation of the hand wheel 86. In the distal end region 87 of the hand wheel 86 a proximal end region 108 of the connecting piece 100 is housed around its entire periphery, towards which the hand wheel 86 can be freely rotated.

The tappet elements 36a, b are housed in the bores 88a, b of the hand wheel 86. The caps 74a, b of the pins 70a, b are arranged radially firmly, whereby the lower parts 78a, b can be moved in a radial direction of the shaft 12 relative to the cap 74a, b and the pins 70a, b are designed to be capable of being longitudinally displaced. The extensions 84a, b of the lower parts 78a, b reach in through the slots 62a, b of the outer tube holder 58 and engage alternately in the grooves 46a, b. The front ends 82a, b of the lower parts 78a, b lie on the outer faces 67a-d of the excenter cams 66a-d and are guided peripherally by them. The radial distance of the outer faces 67a-d of the excenter cams 66a-d from the inner tube holder 40 in the region of the slots 62a, b is hereby measured such that the extensions 84a, b of the pins 70a, b engage fully in grooves 46a, b and almost touch a groove floor. The radial distance of the outer faces 67a-d of the excenter cams 66a-d from the inner tube holder 40 in the region of the sections 68a-d which do not bear against the slots 62a, b is on the contrary measured such that the extensions 84a, b of the pins 70a, b are raised out of the grooves 46a, b and bear against an outer face 109 of the outer tube holder 58. The first tappet element 36a is guided laterally through the first and second guide elements 69a, b and the second tappet element 36b is guided through the second and third guide elements 69b, c, preventing axial tilting of both tappet elements 36a, b.

The tappet elements 36a, 36b can also be designed in one piece instead of in two parts with spring loading, wherein the tappet elements 36a, 36b can be engaged and disengaged with the inner shaft by means of positive control. Such positive control can be brought about for example by guides which can move the tappet elements 36a, 36b in the direction of the axis or away from the axis by engaging tappet elements 36a, 36b from the side.

Arranged between the outer tube holder 58 and the inner tube 38 on both sides of an inner tube opening 110 passing through the inner tube 38 and on both sides of an outer tube holder opening 112, passing through the outer tube holder 58 and arranged radially adjacent in the assembled state of the medical instrument 10, are two fully circumferential seals 114a, b, which improve the seal between the adjoining components of the medical instrument 10. Between the connecting piece 100 and the outer tube holder 58 the coupling element 14 also has another fully circumferential seal 116 which is arranged in a radial direction of the shaft 12 adjacent to the seal 114a. Another fully circumferential seal 118 is arranged between the outer tube holder 58 on the distal side of the first guide element 69a, the connecting piece 100 and the distal end region 87 of the hand wheel 86. In the region of the proximal end region 94 of the outer tube holder 58 are furthermore arranged two more fully circumferential seals 120, 122 which seal off the outer tube holder 58 or the connecting element 104 connected therewith with respect to the handle 16 and seal off the flange 51 of the inner tube holder 40 with respect to the outer tube holder 58. The seals 114a, b, 116-122 are made of rubber.

FIGS. 8A-C and FIGS. 9A-C are perspective views and cross-sectional views of the handle 16 or rotary mechanism in three different relative rotary positions 124-128 of the inner shaft 26 and of the outer shaft 28. The associated relative rotary angles of the inner shaft 26 and outer shaft 28 are approximately 0°, 90° and 180°.

Figure 8A:
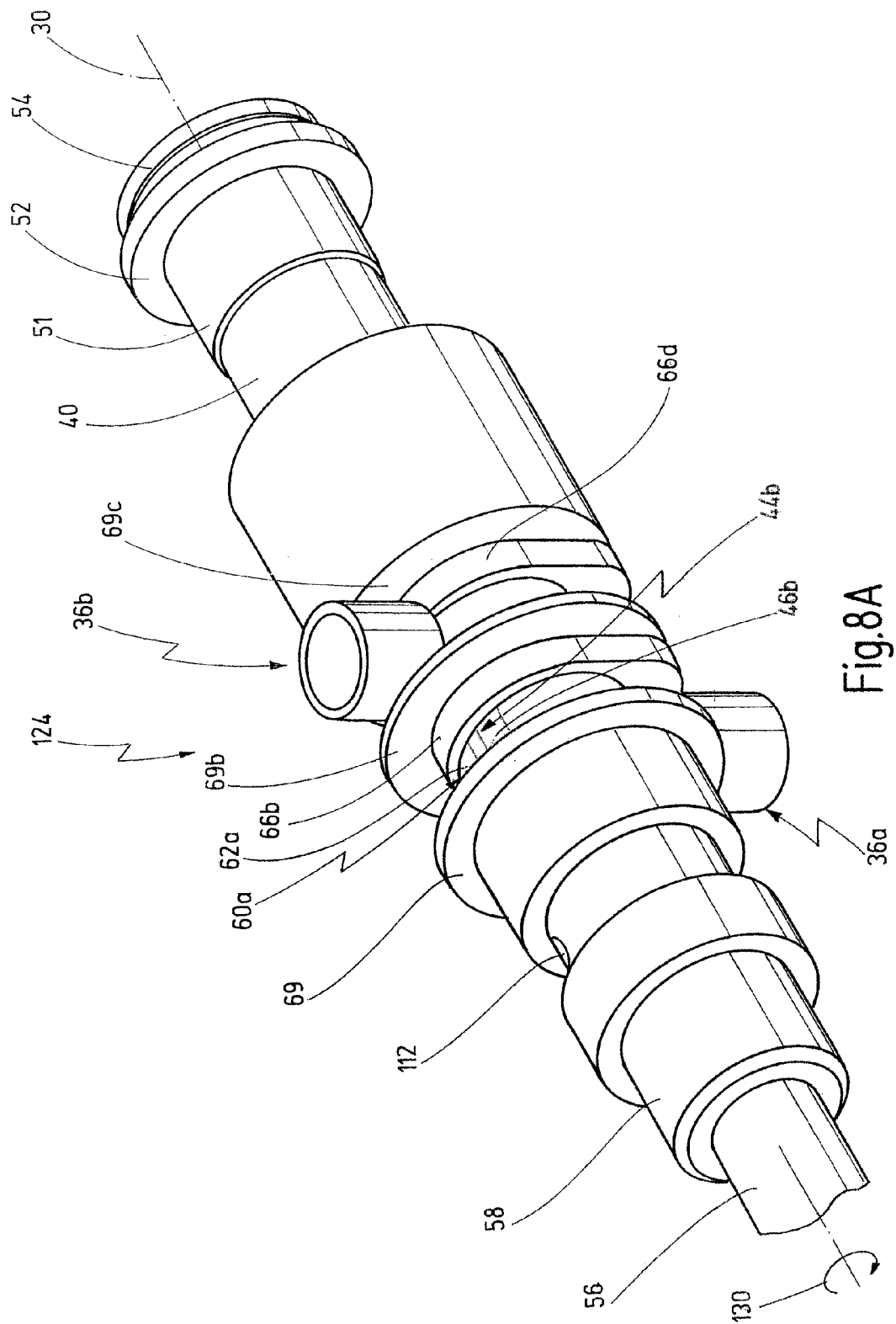
FIGS. 8A-C show perspective views of the handle in FIG. 2 in different rotary positions.
Figure 9A:
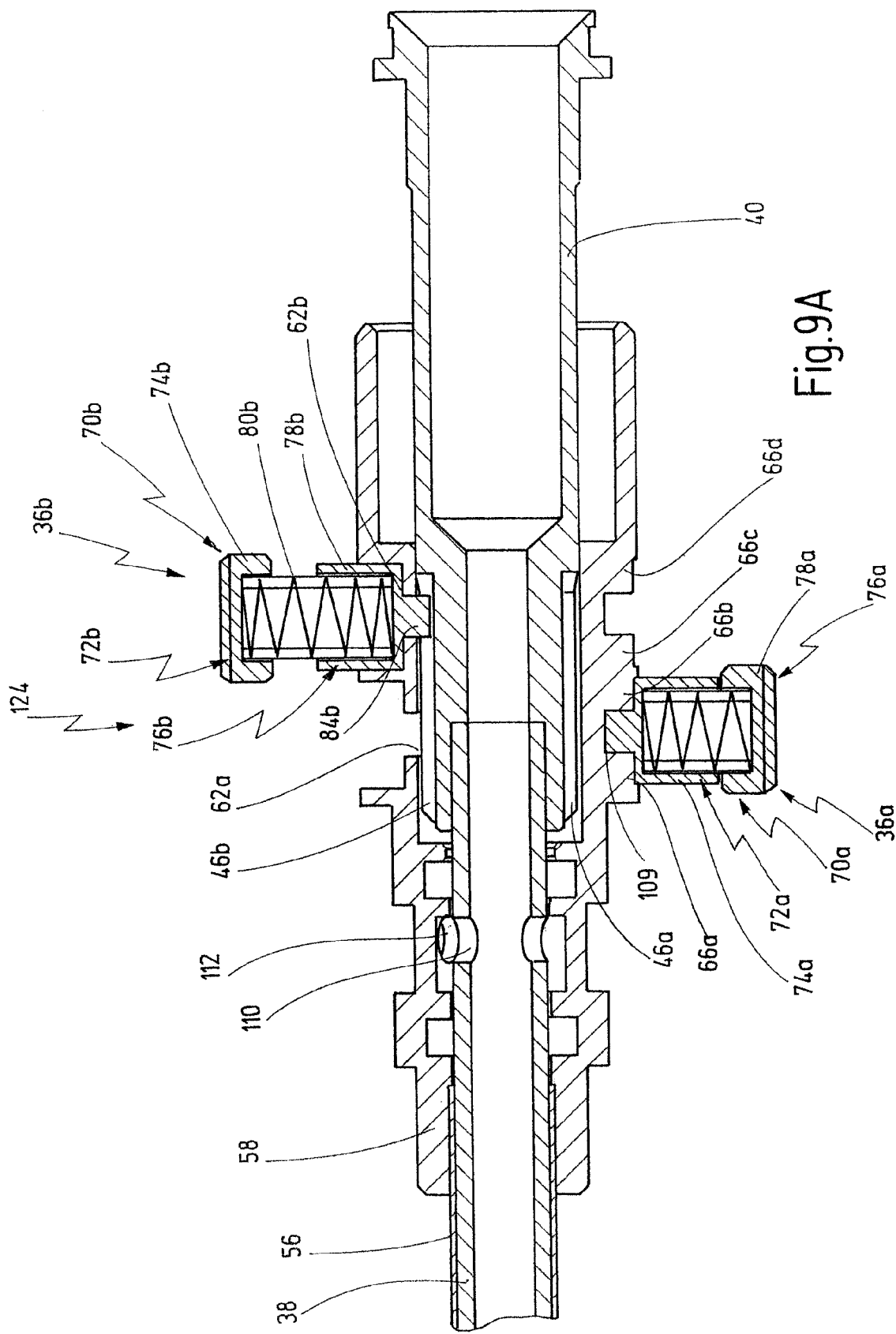
FIGS. 9A-C show cross-sectional views of the handle in FIGS. 8A-C in the different rotary positions.

In the first rotary position 124 illustrated in FIGS. 8A and 9A the extension 84b of the pin 70b engages through the slot 62b fully in the groove 46b of the inner tube holder 40, while due to the radial distance of the excenter cams 66a, b the extension 84a of the pin 70a sits on the outer face 109 of the outer tube holder 58 and has no connection to the inner tube holder 40. The lower part 78a of the pin 70a is pressed in towards the cap 74a which is arranged such that it is radially fixed, so that the pin 70a, which can be longitudinally displaced, has its minimum length. The pin 70b on the other hand has its maximum length so that its lower part 78b is at a maximum distance from the cap 74b.

Figure 8B:
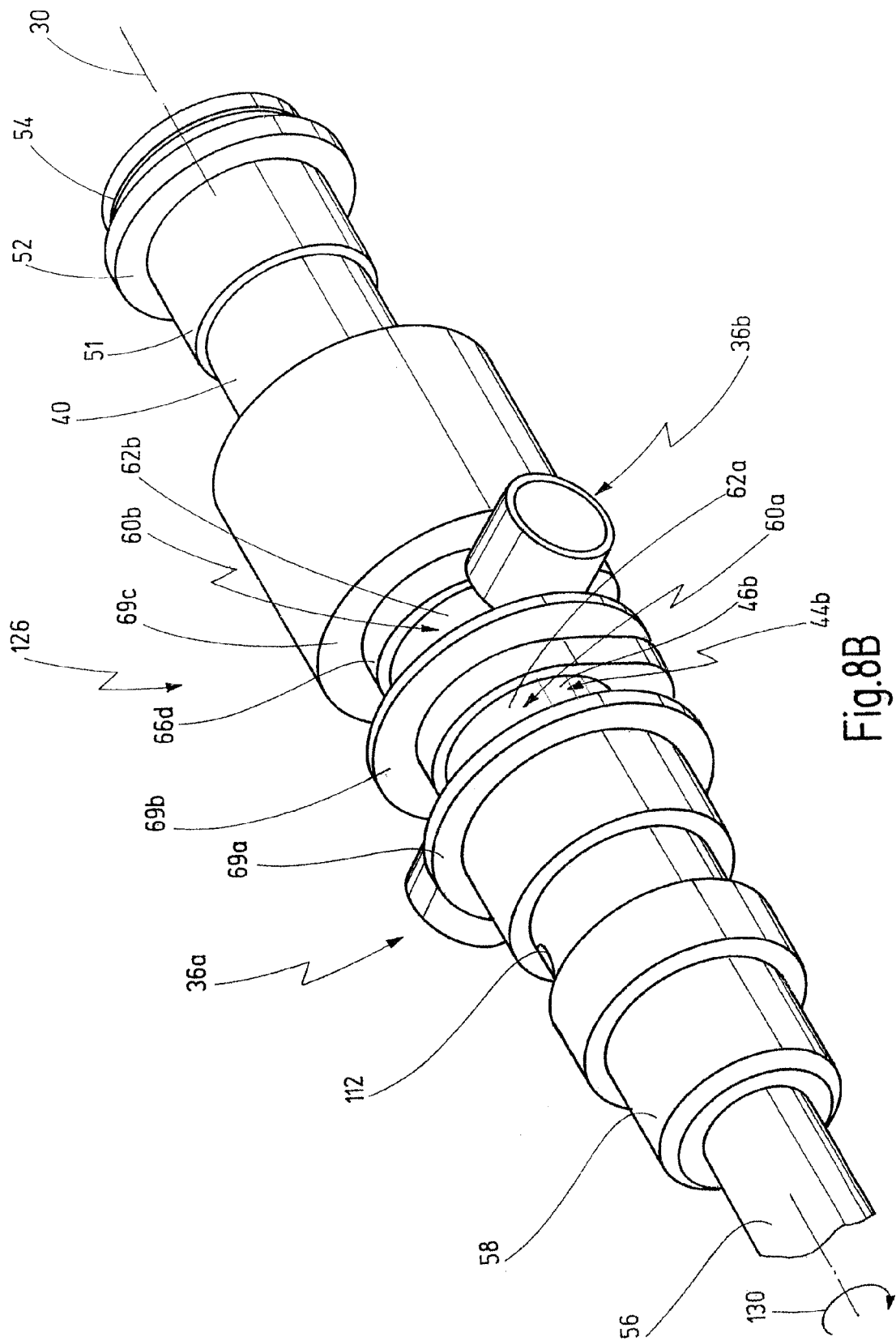
Figure 9B:
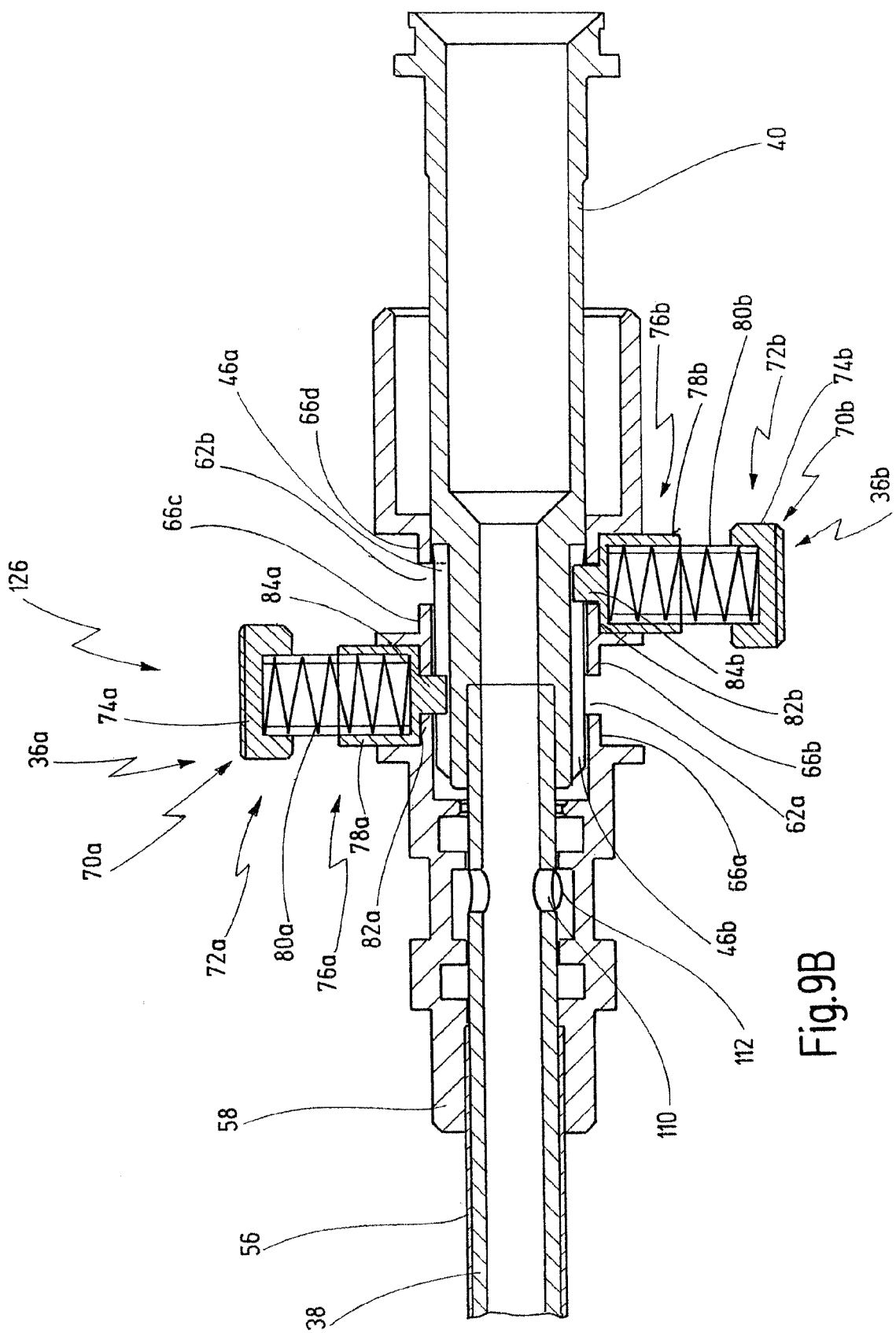

If the hand wheel 86 is rotated for example in the direction of an arrow 130, the second rotary position 126 is reached, in which the inner shaft 26 is rotated relative to the outer shaft 28 by an angle of approximately 90° (cf. FIGS. 8B, 9B). In this rotary position 126 the pins 70a, b with their extensions 84a, b reach in through the slots 62a, b and at the same time are both engaged with the grooves 46a, b. During the described rotary movement of the hand wheel 86 the pin 70a is rotated along the outer face 109 of the outer tube holder 58 until it reaches a slot end of the slot 62a pointing towards the said pin. Due to the decreasing radial distance of the outer faces 68a, b of the excenter cams 66a, b from the inner tube holder 40, the pin 70a engages with the groove 46a precisely at the moment of the second rotary position 126. During the rotary movement of the hand wheel 86 from the first rotary position 124 to the second rotary position 126, the pin 70b is also rotated with it in the direction of the arrow 130 so that the pin 70b moves along the slot 62b. Throughout this rotary movement the extension 84b of the pin 70b is engaged with the groove 46b and, due to the radially varying configuration of the excenter cams 66c, d, is not yet lifted out of the groove 46b. The rotary movement of the inner shaft 26 relative to the outer shaft 28 is caused by the pin 70b. The pins 70a, b have, in the rotary position 126, approximately the same length, since the spring 80a of the pin 70a in comparison to the rotary position 124 is relaxed and the pin 70b still substantially retains its length.

Figure 8C:
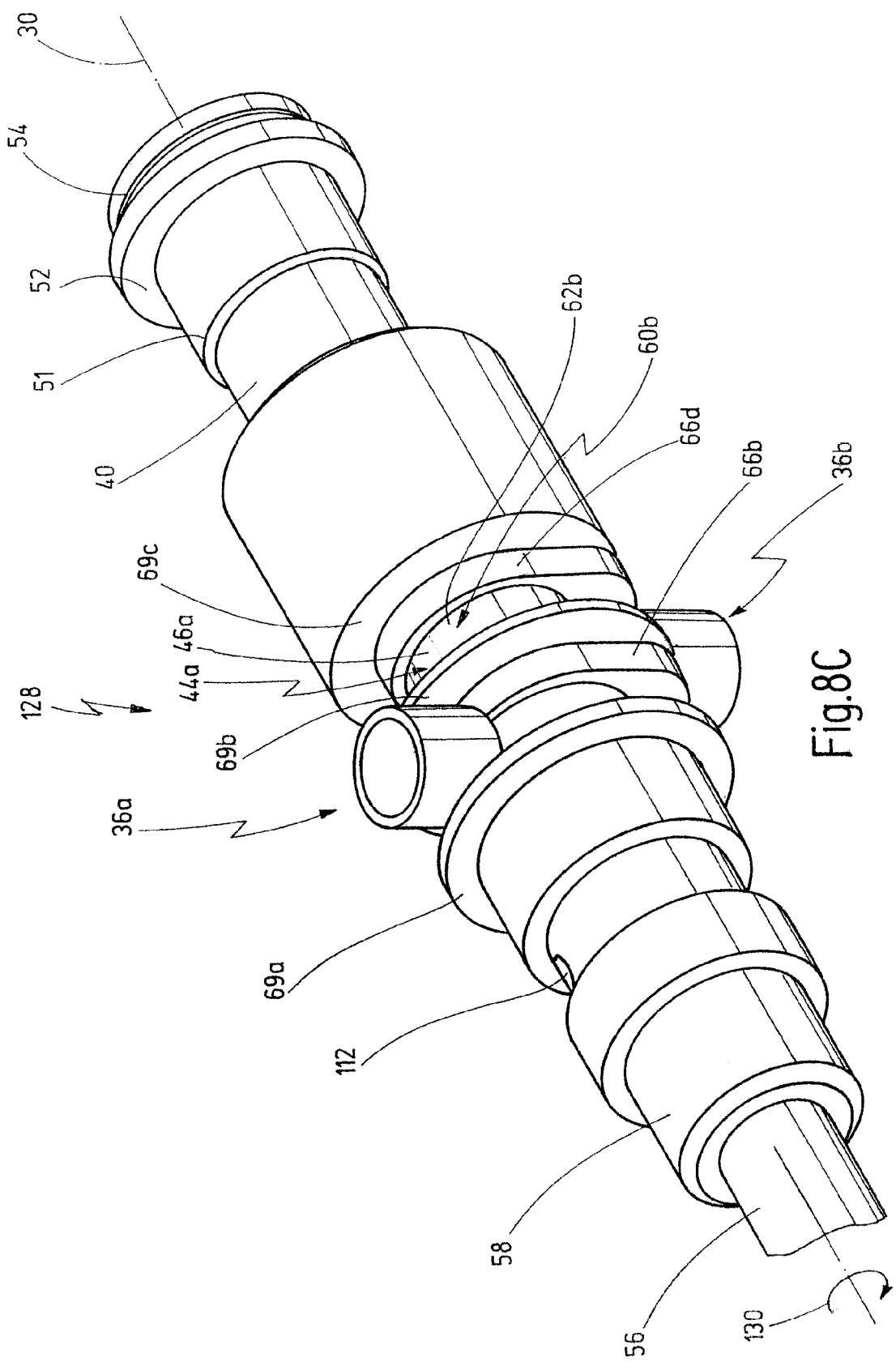
Figure 9C:
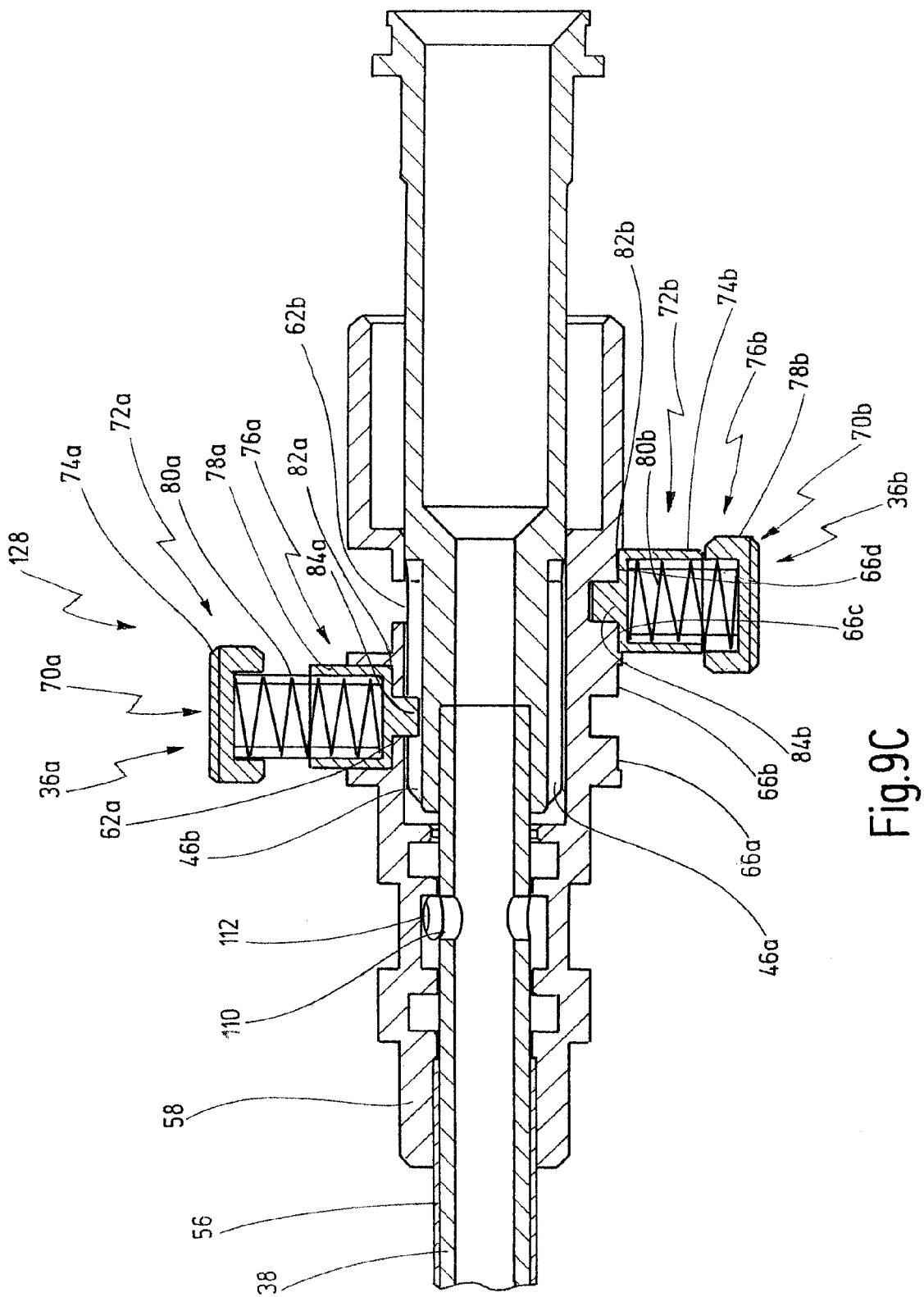

When the hand wheel 86 is turned further by approximately 90° in the direction of the arrow 130, the third relative rotary position 128 of the inner shaft 26 and of the outer shaft 28 is reached (cf. FIGS. 8C, 9C). At this point the pin 70a engages fully with the groove 46a, whereas the pin 70b is lifted out of the groove 46b and bears on the outer tube holder 58 on the outside. In the third rotary position 128 the pin 70a now has its maximum length, while the pin 70b is compressed to the maximum.

Each tappet element 36a, b accordingly transfers a semi-peripheral rotation of approximately 180° to the inner shaft 26 such that a relative rotation around the entire circumference of the inner shaft 26 and of the outer shaft 28 through 360° is caused by two partial rotations of the inner shaft 26 in the same direction of rotation which are respectively transferred by one of the two tappet elements 36a, b. Due to the symmetrical configuration of the torque transmission mechanics 32, the inner shaft 26 can be rotated relative to the outer shaft 28 in both directions of rotation about the longitudinal axis 30 of the medical instrument 10.

In a further exemplary embodiment the inner tube holder 40 has only one groove 46a. The tappet elements 36a, b are arranged offset in the longitudinal direction 30 of the medical instrument 10 and axially adjacent to one another. For this purpose the bores 88a, b of the hand wheel 86 are arranged offset in the longitudinal direction 30 and axially adjacent to one another. The approximately semi-peripheral slots 62a, b and the control cams 64a-d of the outer tube holder 58 are also arranged in the longitudinal direction 30 and offset with respect to one another peripherally by approximately 180° so that the tappet elements 36a, b again engage alternately with the groove 40 to transfer the rotary movement of the hand wheel 86 alternately to the inner tube holder 40.

If the medical instrument 10 has more than two tappet elements 36, for example n tappet elements 36, the relative rotation of the inner shaft 26 and of the outer shaft 28 is transferred in each case by a tappet element 36 engaging with the inner shaft 26. Here, when viewed peripherally, the tappet elements 36 can be arranged offset with respect to one another by an angle of approximately 360°/n, while the outer tube holder has n openings 60 arranged axially adjacent and the inner tube holder 40 has n recesses 44 offset with respect to one another peripherally by an angle of approximately 360°/n. In the event where the openings 60 are designed as slots 62 they have an opening range of approximately 360°/n. The control cams 66 of the outer tube holder 58 are arranged axially adjacent and, over an angular range of approximately 360°(n−1)/n, their outer faces 67 have a radial distance from the inner tube holder 40 such that the respective tappet element 36 is engaged with the respective recess 44 only over a remaining angular range of approximately 360°/n.

It is likewise possible that the n tappet elements 36 are arranged offset in the longitudinal direction 30 of the medical instrument 10 and axially adjacent, while the n openings 60 of the outer tube holder 58 are arranged correspondingly offset by an angle of approximately 360°/n when viewed in the longitudinal direction 30 and peripherally. The openings 60 designed as slots 62 hereby have an opening angle of approximately 360°/n. The inner tube holder 40 further has preferably only one recess 44 in which the tappet elements 36 alternately engage. When viewed peripherally, the control cams 66 of the outer tube holder 58 are arranged offset with respect to one another by an angle of approximately 360°/n and their outer faces 67, over an angular range of approximately 360°(n−1)/n, in each case have a radial distance from the inner tube holder 40 such that the tappet elements 36 in this angular range can be disengaged from the inner shaft 26.

What is claimed is:

1. A medical instrument, comprising:
   a shaft having an outer shaft and an inner shaft, said outer shaft enclosing said inner shaft, said outer shaft having a longitudinal axis and a proximal end region,
   an actuator for rotating said inner shaft about said longitudinal axis relative to said outer shaft, said actuator being arranged at said proximal end region of said outer shaft and being rotatable about said longitudinal axis,
   at least two tappet elements operatively connected with said actuator for transfer-ring a rotary movement of said actuator to said inner shaft, said at least two tappet elements being engaged alternatingly with respect to one another with said inner shaft for transferring said rotary movement of said actuator to said inner shaft, said at least two tappet elements reaching through peripherally limited openings in said proximal end region of said outer shaft, said openings being offset with respect to one another in direction of said longitudinal axis.

2. The instrument of claim 1, wherein adjacent to said openings of said outer shaft said outer shaft has control cams for said at least two tappet elements, which control cams serve for alternate disengagement and engagement of said at least two tappet elements with said inner shaft.

3. The instrument of claim 2, wherein said control cams have a full circumference and are distanced radially from said inner shaft in sections which are not immediately adjacent to said openings such that said at least two tappet elements are disengaged from said inner shaft.

4. The instrument of claim 1, wherein said at least two tappet elements are arranged peripherally offset.

5. The instrument of claim 1, wherein said at least two tappet elements are designed in each case in two parts, wherein a first tappet element part and a second tappet element part of said at least two tappet elements are supplied with resilient force, wherein said first tappet element part and said second tappet element part can be moved in a radial direction of said shaft relative to one another.

6. The instrument of claim 1, wherein said at least two tappet elements extend in a radial direction with respect to said shaft.

7. The instrument of claim 1, wherein said inner shaft has at least one recess for accommodating said at least two tappet elements.

8. The instrument of claim 7, wherein said recess is designed as a groove running in direction of said longitudinal axis.

9. The instrument of claim 1, wherein said openings of said outer shaft are designed as slots.

10. The instrument of claim 1, comprising exactly said two tappet elements, wherein said openings of said outer shaft are designed approximately semi-peripherally.

11. The instrument of claim 10, wherein said two tappet elements are arranged offset peripherally by approximately 180 degree.

12. The instrument of claim 10, wherein said two tappet elements are arranged axially adjacent.

13. A medical instrument, comprising:
    a shaft having an outer shaft and an inner shaft, said outer shaft enclosing said inner shaft, said outer shaft having a longitudinal axis and a proximal end region,
    an actuator for rotating said inner shaft about said longitudinal axis relative to said outer shaft, said actuator being arranged at said proximal end region of said outer shaft, at least two tappet elements operatively connected with said actuator for transferring a rotary movement of said actuator to said inner shaft, said at least two tappet elements being engaged alternatingly with respect to one another with said inner shaft for transferring said rotary movement of said actuator to said inner shaft, said at least two tappet elements reaching through peripherally limited openings in said proximal end region of said outer shaft, said openings being offset with respect to one another in direction of said longitudinal axis, said outer shaft having control cams adjacent to said openings of said outer shaft for said at least two tappet elements, said control cams serve for alternate disengagement and engagement of said at least two tappet elements with said inner shaft, said control cams having a full circumference and are distanced radially from said inner shaft in sections which are not immediately adjacent to said openings such that said at least two tappet elements are disengaged from said inner shaft.

14. The instrument of claim 13, wherein said at least two tappet elements are arranged peripherally offset.

15. The instrument of claim 13, wherein said at least two tappet elements are designed in each case in two parts, wherein a first tappet element part and a second tappet element part of said at least two tappet elements are supplied with resilient force, wherein said first tappet element part and said second tappet element part can be moved in a radial direction of said shaft relative to one another.

16. The instrument of claim 13, wherein said at least two tappet elements ex-tend in a radial direction with respect to said shaft.

17. The instrument of claim 13, wherein said inner shaft has at least one recess for accommodating said at least two tappet elements.

18. The instrument of claim 17, wherein said recess is designed as a groove running in direction of said longitudinal axis.

19. The instrument of claim 13, wherein said openings of said outer shaft are designed as slots.

20. The instrument of claim 13, comprising exactly said two tappet elements, wherein said openings of said outer shaft are designed approximately semi-peripherally.

21. The instrument of claim 20, wherein said two tappet elements are arranged offset peripherally by approximately 180 degree.

22. The instrument of claim 20, wherein said two tappet elements are arranged axially adjacent.

* * * * *